United States Patent
Abbracchio et al.

(10) Patent No.: US 9,879,030 B2
(45) Date of Patent: Jan. 30, 2018

(54) GPR17 RECEPTOR MODULATORS

(75) Inventors: Maria Pia Abbracchio, Milan (IT); Mario Alberto Battaglia, Genoa (IT); Ivano Eberini, Milan (IT); Marta Fumagalli, Milan (IT); Chiara Parravicini, Milan (IT); Cristina Sensi, Milan (IT); Paola Zaratin, Genoa (IT)

(73) Assignees: UNIVERSITA' DEGLI STUDI DI MILANO, Milan (IT); FONDAZIONE ITALIANA SCLEROSI MULTIPLA—FISM ONLUS, Genoa (IT)

( * ) Notice: Subject to any disclaimer, the term of this patent is extended or adjusted under 35 U.S.C. 154(b) by 0 days.

(21) Appl. No.: 14/399,518

(22) PCT Filed: May 9, 2012

(86) PCT No.: PCT/EP2012/058500
§ 371 (c)(1),
(2), (4) Date: Dec. 24, 2014

(87) PCT Pub. No.: WO2013/167177
PCT Pub. Date: Nov. 14, 2013

(65) Prior Publication Data
US 2015/0141410 A1    May 21, 2015

(51) Int. Cl.
| | |
|---|---|
| *C07D 243/12* | (2006.01) |
| *C07D 249/12* | (2006.01) |
| *C07D 487/04* | (2006.01) |
| *A61K 31/4196* | (2006.01) |
| *A61K 31/551* | (2006.01) |
| *C07D 495/14* | (2006.01) |
| *A61K 31/454* | (2006.01) |
| *A61K 31/4725* | (2006.01) |
| *A61K 31/4741* | (2006.01) |
| *A61K 31/519* | (2006.01) |
| *A61K 31/5513* | (2006.01) |
| *A61K 45/06* | (2006.01) |
| *C07D 243/16* | (2006.01) |
| *C07D 491/056* | (2006.01) |

(52) U.S. Cl.
CPC ........ *C07D 495/14* (2013.01); *A61K 31/4196* (2013.01); *A61K 31/454* (2013.01); *A61K 31/4725* (2013.01); *A61K 31/4741* (2013.01); *A61K 31/519* (2013.01); *A61K 31/5513* (2013.01); *A61K 45/06* (2013.01); *C07D 243/12* (2013.01); *C07D 243/16* (2013.01); *C07D 249/12* (2013.01); *C07D 487/04* (2013.01); *C07D 491/056* (2013.01)

(58) Field of Classification Search
CPC .. C07D 243/12; C07D 249/12; C07D 487/04; A61K 31/4196; A61K 31/551
See application file for complete search history.

(56) References Cited

U.S. PATENT DOCUMENTS

| | | | |
|---|---|---|---|
| 5,939,462 A | 8/1999 | Connell et al. | |
| 7,501,405 B2 * | 3/2009 | Kampen | A61K 31/519 514/211.01 |
| 2009/0118135 A1 | 5/2009 | Reed et al. | |
| 2009/0163545 A1 * | 6/2009 | Goldfarb | A61K 31/122 514/312 |
| 2011/0112098 A1 * | 5/2011 | Dariavach | A61K 31/167 514/237.2 |
| 2011/0257184 A1 | 10/2011 | Qu et al. | |

FOREIGN PATENT DOCUMENTS

| | | |
|---|---|---|
| RU | 1596719 A1 | 9/1996 |
| WO | 2004005323 A2 | 1/2004 |
| WO | 2006007864 A1 | 1/2006 |
| WO | 2006045476 A2 | 5/2006 |
| WO | 2007061923 A2 | 5/2007 |
| WO | 2010025308 A2 | 3/2010 |
| WO | 2010111711 A2 | 9/2010 |
| WO | 2010111713 A2 | 9/2010 |
| WO | 2010151797 A2 | 12/2010 |

OTHER PUBLICATIONS

Micael Jacobsson, Magnus Garedal, Johan Schultz and Anders Karlen, Identification of Plasmodium falciparum Spermidine Synthase Active Site Binders through Structure-Based Virtual Screening, Journal of Medicinal Chemistry, 2008, pp. 2777-2786, vol. 51, 10.1021/jm7016144, American Chemical Society, Sweden.

\* cited by examiner

*Primary Examiner* — Bruck Kifle
(74) *Attorney, Agent, or Firm* — Robert E. Alderson, Jr.

(57) ABSTRACT

Chemical compounds are provided which act on GPR17 receptors and are useful in the treatment or amelioration of chronic and/or acute neurodegenerative diseases, such as multiple sclerosis, inflammatory diseases, pathologies involving the immune system, cardiovascular diseases, and renal diseases.

4 Claims, 2 Drawing Sheets

Figure 1A

GPR17 RECEPTOR MODULATORS

CROSS-REFERENCE TO RELATED APPLICATION

This application is a National Phase Application of PCT International Application No. PCT/EP2012/058500, International Filing Date, May 9, 2012, which is hereby incorporated by reference in its entirety.

FIELD OF THE INVENTION

The present inventions generally relates to chemical compounds acting through GPR17 receptor for use in the treatment of diseases, in particular for use in chronic and/or acute neurodegenerative diseases, preferably Multiple Sclerosis, inflammatory diseases, pathologies involving the immune system, cardiovascular diseases, renal diseases.

BACKGROUND OF THE INVENTION

The seven-helix transmembrane G protein-coupled receptor (GPCR) family, encompassing more than 1,000 putative members, is crucially involved in cell-to-cell communication, in the response to environmental factors and hormones, and in the regulation of key cellular functions such as growth, differentiation and death. Due to such central roles, the malfunctioning of GPCRs (or of their signaling cascades) is associated to disease. A large majority of currently marketed drugs (including widely utilized anti-hypertensive, anti-thrombotic, anti-psychotic, anti-asthmatic and anti-ulcer drugs) indeed act through GPCRs.

Among all GPCRs, GPR17, is located at intermediate phylogenetic position between known purinergic P2Y and cysteinyl-leukotrienes (cysLTs) receptors (CysLTRs). Already characterized P2Y receptors and CysLTRs are activated, respectively, by extracellular nucleotides (Abbracchio et al., 2006) or cysLTs (Brink et al. 2003), two distinct families of inflammatory molecules acting as "danger signals" (Lecca et al., 2008), that sense damage in tissues and activate local reparative processes. These endogenous signaling molecules and their receptors mediate immune responses and ischemic/inflammatory conditions, including stroke and several currently incurable neurodegenerative diseases (Abbracchio et al., 2009). GPR17 signals through G(i) and inhibition of adenylyl cyclase and it has been previously shown that GPR17 responds to both uracil nucleotides and cysLTs (Ciana et al. 2006; Lecca et al., 2008; Pugliese et al. 2009). By employing a variety of in vivo rodent models of acute and chronic nervous system degenerative disorders, GPR17 has been validated as a novel target for the design of new drugs of potential use in human diseases characterized by neuronal and myelin dysfunction, including stroke, brain and spinal cord trauma and multiple sclerosis (Lecca et al. 2008; Ceruti et al. 2009; Chen et al. 2009). In a rat brain focal ischemia model, the selective in vivo knock down of GPR17 by anti-sense technology or P2Y/CysLTRs antagonists reduced progression of ischemic damage (WO2006/045476). Moreover, the involvement of GPR17 in the transition from oligodendrocyte precursors to mature oligodendrocytes expressing a myelinating phenotype has been demonstrated (Lecca et al., 2008; Chen et al. 2009; Fumagalli et al., 2011). These mature oligodendrocytes are able to repair a myelinic damage, by restoring the damaged myelinic envelope en-wrapping neuronal axons. All the published experimental data on GPR17 have been obtained using already available agonists and, in most cases, antagonists that have been purposely developed for other GPCRs.

Multiple Sclerosis (MS) is a chronic progressive disorder. It is an inflammatory disease in which the fatty myelin sheaths around the axons of the brain and spinal cord are damaged, leading to demyelination and scarring as well as a broad spectrum of signs and symptoms. MS is one of the central nervous system pathology with the largest diffusion. It affects about 1.3 million persons in the world, of which 400.000 in Europe. This incidence is worsened by the fact that MS affects still young peoples, who need chronic treatments, with a strong social and economical impact. The pharmacological treatments currently available are symptomatic and are not able to counteract MS progression. Immunomodulators are actually used and revealed a certain grade of effectiveness in acute treatments. However, they fail to solve the pathology. Moreover, all of the currently available therapeutics display significant side effects, both local and systemic.

Given the role played by GPR17 in the myelination process (Lecca et al. 2008, Chen et al. 2009; Fumagalli et al., 2011) and in the reduction of ischemic damage progression, there is the strong need to identify molecules capable to specifically bind said GPR17 receptor to be used as novel therapeutics in ischemia and MS or in any other condition characterized by demyelination. It is worth to note that for many of the conditions characterized by demyelination, such as schizophrenia, depression, Alzheimer's Disease, Parkinson's Disease, amyotrophic lateral sclerosis and Huntington's Disease, no curative therapy are currently available. Up to now, only non specific compounds have been tested on GPR17. In particular, CysLTRs antagonists have been used, selected from Montelukast, Pranlukast, Zafirlukast. These compounds are commercially available for asthma therapy. Alternatively, P2Y receptor antagonist have been used. Among these, Cangrelor and Ticagrelor. Ticagrelor has been approved by EMEA and FDA as a platelet aggregation inhibitor.

Rational drug development is a process to develop lead molecules, not by randomly screening thousands of molecules in the blind hope of finding one that shows the desired activity, but rather by deducing the active site of the target and devising a chemical that interacts with that site in the appropriate manner.

A crystallographic structure of GPR17 is not available so far. However, the crystallographic structures of the human CXC chemokine receptor type 4 (CXCR4) (Wu et al. 2010) is known and it is of particular interest for the purpose of the here claimed invention. In fact, the G protein-coupled chemokine receptor CXCR4 has been demonstrated to be phylogenetically and structurally very close to GPR17. CXCR4 crystallographic structure revealed a consistent homodimer with an interface including helices V and VI that may be involved in regulating signaling (Wu et al. 2010). The location and shape of the ligand-binding sites differ from other G protein-coupled receptors and are closer to the extracellular surface.

Here we describe families of compounds specifically able to interact with GPR17 receptor. Compounds and pharmaceutically acceptable salts thereof are useful in the treatment of pathological conditions such as stroke, heart disease, heart failure, high blood pressure, neurodegenerative diseases selected from, for example, Huntington's Disease, motor neuron diseases, leukodystrophies and MS.

SUMMARY OF THE INVENTION

The present invention is directed to families of compounds able to interact with GPR17 binding site, thus ameliorating a panel of pathologic phenotypes, in particular chronic and/or acute neurodegenerative diseases, preferably Multiple Sclerosis, pathologies involving the immune system, cardiovascular diseases, renal diseases.

BRIEF DESCRIPTION OF THE FIGURES

FIG. 1A: cys configuration in the chains of a panel of GPCRs, among which GPR17 and CXCR4.

DETAILED DESCRIPTION

Figure 1A:
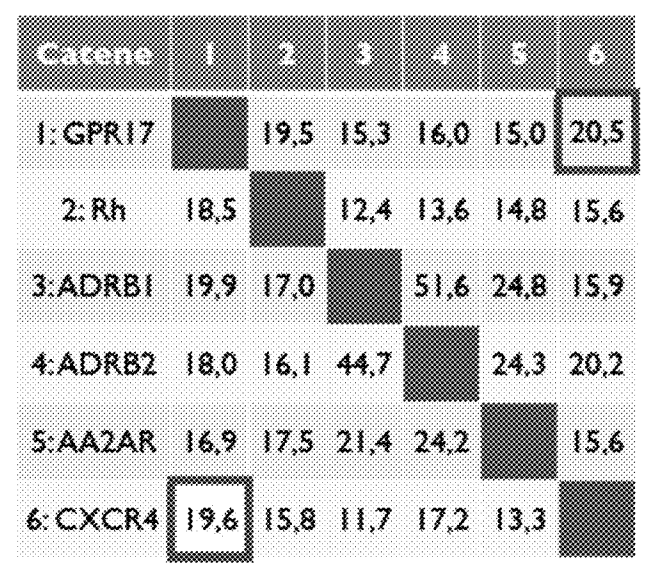
Figure 1B:
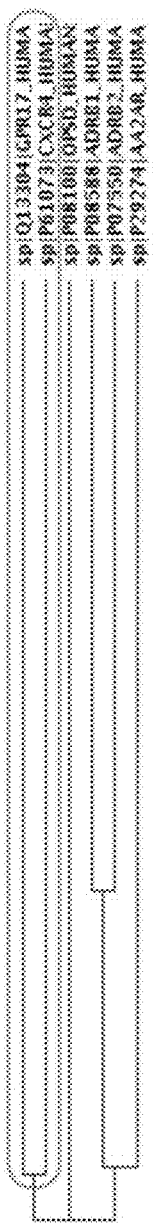
FIG. 1B: alignment proposed for a panel of GPCRs.

A 3-D molecular model of GPR17 embedded in a solvated phospholipids bilayer and refined by molecular dynamics simulations has been obtained (Parravicini et al. 2008). The molecular dynamics simulations indicate that GPR17 nucleotide binding pocket is similar to that described for the other P2Y receptors, although only one of the three basic residues that have been typically involved in ligand recognition is conserved (Arg255). The binding pocket is enclosed between the helical bundle and covered at the top by EL2. Driving interactions are H-bonds and salt bridges between the 6.55 and 6.52 residues and the phosphate moieties of the ligands. An "accessory" binding site in a region formed by the EL2, EL3 and the Nt was also found. Following the disclosure of the crystallographic structure of the CXCR4 receptor, the GPR17 binding site model has been implemented. By comparing CXCR4 crystallographic structure with the in silico modeled GPR17 receptor previously obtained by using the above mentioned multiple template approach (Parravicini et al., 2010), in which the extracellular loops of the receptor were modeled making reference to the most similar parts of all the class-A GPCRs crystallized so far (Eberini et al., 2011), the authors selected the CXCR4 crystallographic structure as the best template to model each domain of GPR17 receptor. FIG. 1 shows the alignment of a panel of GPCRs available as templates, among which CXCR4: in FIG. 1A, the values in each column represent the percentage of the chain's residues which are paired with identical residues in the chains of each row; FIG. 1B shows the resulting phylogenetic tree. As suggested by the alignment, the best template for GPR17 is considered to be CXCR4.

Thanks to this model, compounds able to interact with GPR17 receptor in an optimized manner, both from a geometric and from an energetic point of view, have been identified.

In one embodiment, the present invention is related to compounds of formula (I)

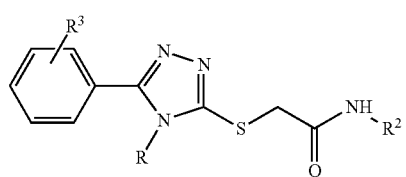

(I)

wherein R is H, a linear or branched C1-C4 alkyl, a linear or branched C1-C4 alkyl phenyl optionally substituted, a phenyl optionally substituted; $R^2$ is H, a linear or branched C1-C4 alkyl, a saturated or unsaturated mono, bi or tricycle having from 3 to 16 members optionally substituted and eventually containing from 1 to 4 heteroatoms selected from N, O, S; $R^3$ is H, a linear or branched C1-C4 alkyl or NHC(O)$R^1$, wherein $R^1$ is a linear or branched C1-C4 alkyl, a saturated or unsaturated mono, bi or tricycle having from 3 to 16 members optionally substituted and eventually containing from 1 to 4 heteroatoms selected from N, O, S.

In a second embodiment, the present invention is related to compounds of formula (II)

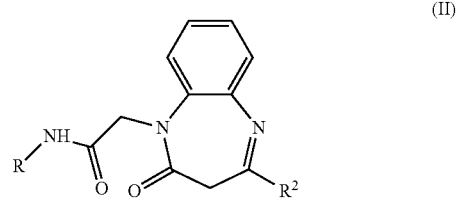

(II)

wherein $R^2$ is H, a C1-C4 linear or branched alkyl, a linear or branched C1-C4 alkyl phenyl optionally substituted, a saturated or unsaturated mono, bi or tricycle having from 3 to 16 members optionally substituted and eventually containing from 1 to 4 heteroatoms selected from N, O, S and R is H, a C1-C4 linear or branched alkyl phenyl optionally substituted, a saturated or unsaturated mono, bi or tricycle having from 3 to 16 members optionally substituted and eventually containing from 1 to 4 heteroatoms selected from N, O, S.

In a third embodiment, what we claim are compounds of formula (III)

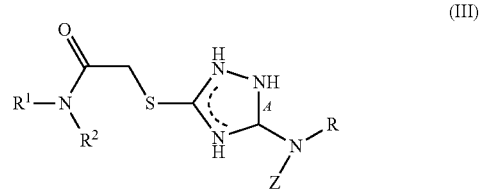

(III)

wherein $R^1$ and $R^2$ are independently H or an optionally substituted phenyl, or $R^1$ and $R^2$ form with the N to which they are linked a saturated or unsaturated mono, bi or tricycle having from 3 to 16 members optionally substituted and eventually containing from 1 to 4 heteroatoms selected from N, O, S; A is a bond or a C; the dotted line represents localized or delocalized double bonds; R is H, C1-C4 aryl, optionally substituted heteroaryl, optionally substituted metylphenyl, —CH$_2$C(O) $R^3$, —CH$_2$C(O) NR$^4$R$^5$; $R^3$ is chosen from optionally substituted alkyl, optionally substituted saturated or unsaturated 3-8 membered cycle eventually containing from to 4 heteroatoms selected from N, O, S, optionally substituted aryl eventually containing from 1 to 4 heteroatoms selected from N, O, S; $R^4$ is chosen from H, optionally substituted alkyl, optionally substituted saturated or unsaturated 3-8 membered cycle eventually containing from 1 to 4 heteroatoms selected from N, O, S, optionally substituted aryl eventually containing from 1 to 4 heteroatoms selected from N, O, S; $R^5$ is chosen from H, optionally substituted alkyl, optionally substituted saturated or unsaturated 3-8 membered cycle eventually containing from 1 to 4 heteroatoms selected from N, O, S, optionally substituted aryl eventually containing from 1 to 4 heteroatoms selected from N, O, S; $R^4$ and $R^5$ taken together with the nitrogen to which they are attached can form an optionally substituted saturated or unsaturated 3-8 membered cycle eventually containing from 1 to 4 heteroatoms selected from N, O, S; Z is H or forms a bicycle with said 5 or 6 membered ring comprising 3 N by closing on a N on said cycle, or, when A is C, by closing on said C, wherein said second ring formed by Z is preferably a 5 membered ring and it is open to fusion.

In the first embodiment, compounds of formula (I)

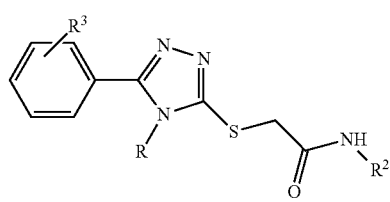

(I)

are preferably selected from the group wherein R is selected from the group comprising H, methyl, ethyl, phenyl, benzyl; $R^2$ is selected from the group comprising H, naphthalene, phenyl, preferably 4Cl-phenyl, benzimidazole, preferably 2-methylbenzimidazole; $R^3$ is preferably selected from the group comprising H, 4-methyl, 4-NHC(O)$R^1$, wherein $R^1$ is phenyl or phenyl mono, bi or tri substituted, wherein said substituents on said phenyl are independently selected from C1-C4 linear or branched alkyl, acetyl, C1-C4 alkoxy, carboxy C1-C4 alkyl, F, Cl, Br, I, triphluoromethyl, nitro, CN.

Preferably, R is H or methyl; $R^2$ is H, naphthalene, phenyl, preferably 4Cl-phenyl, benzimidazole, preferably 2-methylbenzimidazole; $R^3$ is H, 4-methyl, 4-NHC(O)$R^1$, wherein $R^1$ is phenyl, preferably 4Cl-phenyl.

Preferably, the compound is selected from N-Phenyl-2-(5-m-tolyl-2H-[1,2,4]triazol-3-ylsulfanyl)-acetamide, 2-(5-m-tolyl-2H-[1,2,4]triazol-3-ylsulfanyl)-acetamide, N-naphthalen-1-yl-2-(5-m-tolyl-2H-[1,2,4]triazol-3-ylsulfanyl)-acetamide, N-Thiazol-2-yl-2-(5-p-tolyl-4H-[1,2,4]triazol-3-ylsulfanyl)-acetamide, N-(2-Methyl-3H-benzoimidazol-5-yl)-2-(5-phenyl-4H-[1,2,4]triazol-3-ylsulfanyl)-acetamide, N-[4-[5-[[2-[(4-chlorophenyl)amino]-2-oxoethyl]thio]-4-methyl-4H-1,2,4-triazol-3-yl]phenyl]-benzamide. In a most preferred embodiment, said compound is N-[4-[5-[[2-[(4-chlorophenyl)amino]-2-oxoethyl]thio]-4-methyl-4H-1,2,4-triazol-3-yl]phenyl]-benzamide.

In the second embodiment, compounds of formula (II)

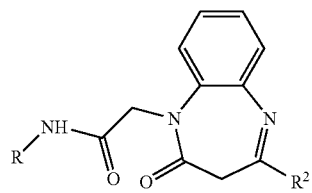

(II)

are preferably selected from the groups wherein $R^2$ is H, phenyl, or a phenyl mono, bi or tri substituted, wherein said substituents on said phenyl are independently selected from methyl, ethyl, methylethyl, acetyl, methoxy, ethoxy, F, Cl, Br, I, carboxyethyl, trifluoromethyl, methylthio, dimetylamino; R is H, phenyl, benzyl, phenylethyl, phenylpropyl, a phenyl mono, bi or tri substituted, wherein said substituents on said phenyl are independently selected from methyl, ethyl, methylethyl, acetyl, methoxy, ethoxy, F, Cl, Br, I, carboxyethyl, trifluoromethyl, methylthio, dimetylamino, or R is 1,3-benzodioxol-5-yl-2,3-dihydro, 2,3-dihydro-1,4-benzodioxin-6-yl, 2-furanylmethyl, cyclohexan.

In a preferred embodiment, $R^2$ is phenyl and R is 2,4 dimethoxyphenyl, benzyl, 2,3-dimethylphenyl or 2,6-dimethylphenyl.

Preferably, the compound is selected from the group comprising N-(2,4-dimethoxyphenyl)-2,3-dihydro-2-oxo-4-phenyl-1H-1,5-Benzodiazepine-1-acetamide, N-Benzyl-2-(2-oxo-4-phenyl-2,3-dihydro-benzo[b][1,4]diazepin-1-yl)-acetamide, N-(2,3-dimethyl-phenyl)-2-(2-oxo-4-phenyl-2,3-dihydro-benzo[b][1,4]diazepin-1-yl)-acetamide, N-(2,6-Dimethyl-phenyl)-2-(2-oxo-4-phenyl-2,3-dihydro-benzo[b][1,4]diazepin-1-yl)-acetamide. The more preferred compound is N-(2,4-dimethoxyphenyl)-2,3-dihydro-2-oxo-4-phenyl-1H-1,5-Benzodiazepine-1-acetamide.

In a third embodiment, the compounds of formula (III)

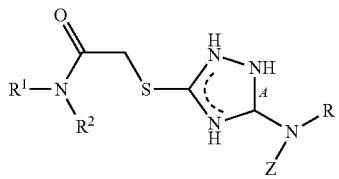

(III)

are preferably selected from the group wherein $R^1$ and $R^2$ are independently H or an optionally substituted phenyl, or $R^1$ and $R^2$ are closed to form with the N to which are linked a 1,2,3,4-tetrahydroquinoline, a 1,2,3,4-tetrahydroisoquinoline, a pirrolidine, a piperidine or a piperazine optionally substituted; A is C and the 6 members ring is an aromatic ring; Z forms a bicycle with said 6 membered ring by closing on A, wherein said second ring formed by Z is a 5 membered ring open to fusion, preferably said 5 membered ring is fused with an optionally substituted phenyl forming a tricycle, preferably said tricycle is a 5H-[1,2,4]triazino[5,6-b]indole optionally substituted; R is H or C1-C4 aryl.

In a preferred embodiment, wherein A is a bond and said ring containing 3 N is a 5 membered ring, said compounds of formula (III) are selected from the group of formula (III)A

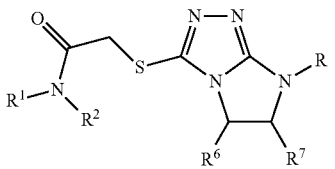

(III)A wherein $R^1$ is H and $R^2$ is an optionally substituted phenyl, or $R^1$ and $R^2$ are closed to form with the N to which are linked a pirrolidine, an optionally substituted pirrolidine, preferably 2-(2,3-dihydro-1,4-benzodioxin-6-yl)-1-pyrrolidinyl, a phenothiazine, an optionally substituted pyridine, a piperidine, an optionally substituted piperidine, preferably a 2-methyl piperidine, a 4-piperidine carboxyester, preferably a 4-piperidine-carboxyethylester, a 4-piperidinecarboxamide, a 3-methylpiperidine, a 4-methyl piperidine, or a 4-phenylmethylpiperidine or a 3-piperidine carboxylic acid or a 4-piperidine carboxylic acid, or a 4-piperidine carboxamide-N-phenyl, or a 3,5-dimethylpiperidine, or a 2,6-dimethylpiperidine, or a 4,5-dihydro-5-phenyl-1H-pyrazol-1-yl, a 4,5-dihydro-5-(4-methoxyphenyl)-3-phenyl-1H-pyrazol- 1-yl, a 2-chloro-10H-phenothiazin-10-yl, a 6,7-dihydrothieno[3,2-c]pyridin-5(4H)-yl, a 4-morpholine, an optionally substituted 4-morpholine, preferably a 2,6-dimethyl-4-morpholine, or a 2-methylmorpholine, an indoline, an optionally substituted indoline, preferably a 1-[2,3-dihydro-5-(1-piperidinylsulfonyl)-1H-indol-1-yl], an isoquinoline, a 1,2,3,4-tetrahydroisoquinoline, a 1,2,3,4-tetrahydroquinoline, a 3,4-dihydro-2-methyl-1(2H)-quinoline, a 1-[3-(2-benzofuranyl)-5-(2-furanyl)-4,5-dihydro-1H-pyrazol-1-yl], a 2H-1,5-benzodiazepin-2-one-4-trifluoromethyl, a 2,3-dihydroindol-1-yl, a 2,3-dimethyl-1H-indol-1yl, a 1-[4-[(3,5-dimethyl-4-isoxazolyl)sulfonyl]-1-piperazinyl], a benzothiazine, a piperazine, an optionally substituted piperazine, preferably a 4-nitrophenylpiperazine or a 2-nitrophenylpiperazine, or a 4-(2-piridinyl)1-piperazine, or a 4-(2-fluorophenil)sulfonyl-1-piperazine or a 4-phenylsulphonil-1-piperazine, or a 3-methylphenyl-1 piperazine, or a 4-(2-methoxyphenyl)piperazine or a 4-phenylpiperazine or a 4-methylphenylpiperazine or a 4-[3-chloro-5-(trifluoromethyl)-2-pyridinyl]-1-piperazine, a 3-trifluoromethylphenyl-1-piperazine, or a 2-fluorophenyl-1-piperazine, a piperidinecarboxamide-N-phenyl, a 1,3,3-trimethyl-6-azabicyclo[3.2.1]oct-6-yl, a 4,5-dihydro-3-(2-naphthalenyl)-5-phenyl-1H-pyrazol-1-yl, a 4-[(2,3-dihydro-1,4-benzodioxin-2-yl)carbonyl]-1-piperazinyl, a pyrrolidone, a 2(1H) quinoxalinone, a [2,3,dihydro-5(1-piperidinylsulfonyl)1H-indol-1yl], a 3,4-dihydro-2(1H)isoquinolinyl, a 3,4-dihydro-2-methyl-1(2H)quinoline, a 3,4-dihydro-6(1-pyrrolidinylsulfonyl)1(2H)quinoline, a 10,11-dihydro-5H-dibenz[b,f]azepin-5-yl, a hexahydro-1H-azepin-1-yl, preferably $R^1$ and $R^2$ are closed to form with the N to which are linked an indoline, a 1,2,3,4-tetrahydroisoquinoline, a 1,2,3,4-tetrahydroquinoline, a piperidine, a pirrolidine; R is H, optionally substituted benzyl or —CH$_2$C(O)NR$^4$R$^5$; R$^4$ is H; R$^5$ is an optionally substituted phenyl or an optionally substituted cycloexane or R$^4$ and R$^5$ form with the nitrogen to which they are attached a pyrrolidine; R$^6$ and R$^7$ are independently H or an optionally substituted phenyl, or R$^6$ and R$^7$ close to form a saturated or unsaturated cycle having from 3 to 8 members optionally substituted and eventually containing from 1 to 4 heteroatoms selected from N, O, S. In a preferred embodiment, R$^6$ and R$^7$ are closed in a cycle forming a tricycle, preferably selected from a 4H-[1,2,4]triazolo[5,1-f]purine-6,8(5H,7H)-dione, preferably a 5,7-dimethyl-4H-[1,2,4]triazolo[5,1-f]purine-6,8(5H,7H)-dione or a 4H-[1,2,4]triazolo[1,5-a]benzimidazole.

Preferably, the compound is selected from the group comprising 3-[[2-(2,3-dihydro-1H-indol-1-yl)-2-oxoethyl]thio]-N-(2-methylphenyl)-9H-1,2,4-Triazolo[4,3-a]benzimidazole-9-acetamide, 2-[9-(4-Chloro-benzyl)-9H-benzo[4,5]imidazo[2,1-c][1,2,4]triazol-3-ylsulfanyl]-1-(3,4-dihydro-1H-isoquinolin-2-ethanone, 2-(9-Benzyl-9H-benzo[4,5]imidazo[2,1-c][1,2,4]triazol-3-ylsulfanyl)-1-pyrrolidin-1-yl-ethanone, 2-[9-(4-Chloro-benzyl)-9H-benzo[4,5]imidazo[2,1-c][1,2,4]triazol-3-ylsulfanyl]-1-pyrrolidin-1-yl-ethanone, 2-[3-(2-Oxo-2-piperidin-1-yl-ethylsulfanyl)-benzo[4,5]imidazo[2,1-c][1,2,4]triazol-9-yl]-1-pyrrolidin-1-yl-ethanone, 2-(9-Benzyl-9H-benzo[4,5]imidazo[2,1-c][1,2,4]triazol-3-ylsulfanyl)-1-(2,3-dihydro-indol-1-yl)-ethanone, 2-(9-Benzyl-9H-benzo[4,5]imidazo[2,1-c][1,2,4]triazol-3-ylsulfanyl)-1-piperidin-1-yl-ethanone, 2-[9-(4-Methyl-benzyl)-9H-benzo[4,5]imidazo[2,1-c][1,2,4]triazol-3-ylsulfanyl]-1-(4-methyl-piperidin-1-yl)-ethanone, 2-{3-[2-(3,4-Dihydro-2H-quinolin-1-yl)-2-oxo-ethylsulfanyl]-benzo[4,5]imidazo[2,1-c][1,2,4]triazol-9-yl}-1-pyrrolidin-1-yl-ethanone, 2-[9-(2-Chloro-benzyl)-9H-benzo[4,5]imidazo[2,1-c][1,2,4]triazol-3-ylsulfanyl]-1-pyrrolidin-1-yl-ethanone, 2-{3-[2-(2,3-Dihydro-indol-1-yl)-2-oxo-ethylsulfanyl]-benzo[4,5]imidazo[2,1-c][1,2,4]triazol-9-yl}-1-pyrrolidin-1-yl-ethanone, 1-(2,3-Dihydro-indol-1-yl)-2-[9-(4-methyl-benzyl)-9H-benzo[4,5]imidazo[2,1-c][1,2,4]triazol-3-ylsulfanyl]-ethanone, 2-{3-[2-(3,4-Dihydro-1H-isoquinolin-2-yl)-2-oxo-ethylsulfanyl]-benzo[4,5]imidazo[2,1-c][1,2,4]triazol-9-yl}-1-pyrrolidin-1-yl-ethanone, 1-(3,4-dihydro-2H-quinolin-1-yl)-2-[9-(4-fluoro-benzyl)-9H-benzo[4,5]imidazo[2,1-c][1,2,4]triazol-3-ylsulfanyl, 2-[9-(2-Fluoro-benzyl)-9H-benzo[4,5]imidazo[2,1-c][1,2,4]triazol-3-ylsulfanyl]-1-pyrrolidin-1-yl-ethanone, N-Cyclohexyl-2-[3-(2-oxo-2-pyrrolidin-1-yl-ethylsulfanyl)-benzo[4,5]imidazo[2,1-c][1,2,4]triazol-9-yl]-acetamide, 2-[9-(4-Fluoro-benzyl)-9H-benzo[4,5]imidazo[2,1-c][1,2,4]triazol-3-ylsulfanyl]-1-pyrrolidin-1-yl-ethanone, 2-(9-Benzyl-9H-benzo[4,5]imidazo[2,1-c][1,2,4]triazol-3-ylsulfanyl)-1-(3,5-dimethyl-piperidin-1-yl)-ethanone, 2-[9-(4-Methyl-benzyl)-9H-benzo[4,5]imidazo[2,1-c][1,2,4]triazol-3-ylsulfanyl]-1-(3-methyl-piperidin-1-yl)-ethanone, 2-[9-(4-Methyl-benzyl)-9H-benzo[4,5]imidazo[2,1-c][1,2,4]triazol-3-ylsulfanyl]-N-(2-piperidin-1-yl-phenyl)-acetamide, 2-(9-Benzyl-9H-benzo[4,5]imidazo[2,1-c][1,2,4]triazol-3-ylsulfanyl)-N-(2-piperidin-1-yl-phenyl)-acetamide. In a preferred embodiment, said compound is 3-[[2-(2,3-dihydro-1H-indol-1-yl)-2-oxoethyl]thio]-N-(2-methylphenyl)-9H-1,2,4-Triazol[4,3-a]benzimidazole-9-acetamide.

The synthetic processes to prepare an exemplificative compound for each one of the claimed families are reported in Examples 1-3 that follow.

For the compound family (I), the proper aryl carboxylate is reacted with hydrazine to obtain an hydrazide which is then reacted with the proper isothiocyanate to give an aryl-4H-1,2,4-triazol-3-thiol. Finally the thiol is reacted with the proper 2-chloroacetamide thus providing the desired product (I).

For the compound family (II) the proper [(2-aminophenyl)amino]methyl 3-oxopropanoate is heated in xylene at reflux to give 1,3-dihydro-2H-1,5-benzodiazepin-2-one, which is then reacted with the proper 2-chloroacetamide to give the desired product (II).

For the compound family (III) the proper heteroaryl thiol is reacted with the proper 2-chloroacetamide to give product (III).

Said families of compounds possess a high affinity for GPR17, significantly higher with respect to endogenous ligands and are not related to ligands known to interact with said receptor, namely agonists and antagonists of P2Y receptor and CysLTRs.

The docking energy evaluated for the here claimed compounds on GPR17 is significantly better than the docking energy evaluated for any other of the compounds tested, as explained in the examples that follow.

The compounds of the present invention revealed useful in treating a variety of pathological conditions associated with GPR17, in particular Multiple Sclerosis and pathologies involving the immune system, cardiovascular diseases, renal diseases.

The methods and techniques for preparing medicaments of a compound of the present invention are well-known in the art. Exemplary pharmaceutical formulations and routes of delivery are described below. One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

Is an object of the present invention a compound selected from the group comprising compounds of formula (I), (II), and (III), as above defined, for use in the treatment of disorders involving GPR17 activation, in particular to treat chronic and/or acute neurodegenerative diseases, inflammatory diseases, pathologies involving the immune system, cardiovascular diseases, renal diseases. Said disorders are selected from the group consisting of Huntington's Disease, Machado-Joseph disease, Spinal and Bulbar muscular Atrophy (SBMA), Dentatorubral Pallidoluysian Atrophy (DRPLA), Fragile X syndrome, Fragile XE mental retardation, Friedreich ataxia, myotonic dystrophy, Spinocerebellar ataxias (types 8, 10 and 12), spinal muscular atrophy (Werdnig-Hoffman disease, Kugelberg-Welander disease), Alzheimer's disease, amyotrophic lateral sclerosis, Parkinson's disease, Pick's disease, and spongiform encephalopathies, age-related memory impairment, agyrophilic grain dementia, corticobasal degeneration, conditions due to developmental dysfunction of the cerebrovasculature, dementia-multi infarct, dementia-subcortical, dementia with Lewy bodies, dementia of human immunodeficiency virus (HIV), dementia lacking distinct histology, dyskinesias (Paroxysmal), dystonias, essential tremor, fronto-temporal dementia, motor neuron diseases, multiple system atrophy, multiple sclerosis and other demyelinating conditions (e.g., leukodystrophies), vascular dementia.

In a preferred embodiment, said compounds are used in ischemia, cerebral trauma and MS.

In a further preferred embodiment, compounds selected from the group of compounds of formula (I), (II) and (III) as above defined are used in the treating of a demyelinizing disease, selected from MS, schizophrenia, depression, Alzheimer's Disease, Parkinson's Disease, Huntington's Disease, SLA or of a neuro-inflammatory disease.

In a further embodiment, said compounds are used in cerebral, cardiac and renal ischemia.

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable for oral and parenteral administration and also include subcutaneous, intramuscular, intravenous and intradermal.

In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with carriers and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In preferred embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose), surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other micro particulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

EXAMPLES

Example 1. Synthesis of N-[4-[5-[[2-[(4-chlorophenyl)amino]-2-oxoethyl]thio]-4-methyl-4H-1,2,4-triazol-3-yl]phenyl]-benzamide of formula (I)

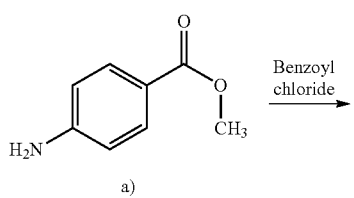

a)

-continued

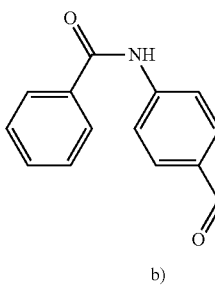
b)

To a solution of a) in DCM/water and KOH was added a solution of an equimolar amount of benzoyl chloride in DCM, to give product b) that was then reacted with NH₂NH₂*H₂O in EtOH thus obtaining the N-[4-(hydrazinylcarbonyl)phenyl]benzamide) c).

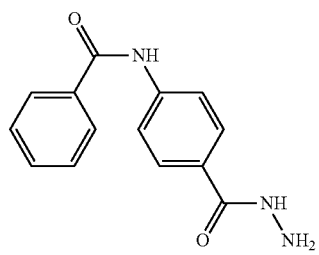
c)

c) was then reacted with MeNCS in EtOH in the presence of KOH, then acidified with HCl thus obtaining the N-[4-(4-methyl-5-sulfanyl-4H-1,2,4-triazol-3-yl)phenyl]benzamide d)

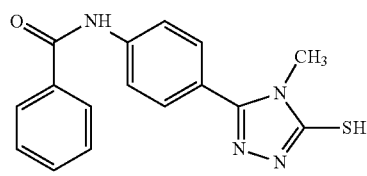
d)

by reacting d) with 2-chloro-N-(4-chlorophenyl)acetamide e) in EtOH, KOH and TEA

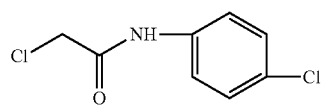
e)

the desired product N-[4-[5-[[2-[(4-chlorophenyl)amino]-2-oxoethyl]thio]-4-methyl-4H-1,2,4-triazol-3-yl]phenyl]-benzamide has been obtained.

Example 2. Synthesis of 1H-1,5-N-(2,4-dimethoxyphenyl)-2,3-dihydro-2-oxo-4-phenyl benzodiazepine-1-acetamide of formula (II)

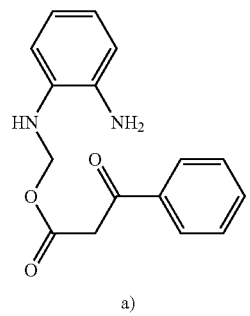 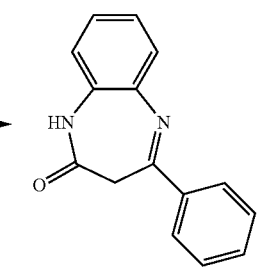
a) b)

[(2-aminophenyl)amino]methyl 3-oxo-3-phenylpropanoate a) has been reacted in xylene at 140° C. to give 4-phenyl-1,3-dihydro-2H-1,5-benzodiazepin-2-one b) that was then reacted with 2-chloro-N-(2,4-dimethoxyphenyl)acetamide c) in K₂CO₃, DMF to give the desired product which is 1H-1,5-N-(2,4-dimethoxyphenyl)-2,3-dihydro-2-oxo-4-phenyl benzodiazepine-1-acetamide. The 2-chloro-N-(2,4-dimethoxyphenyl)acetamide has been obtained by reacting 2,4-dimetoxybenzenamine with chloroacetyl chloride in MeCN at reflux.

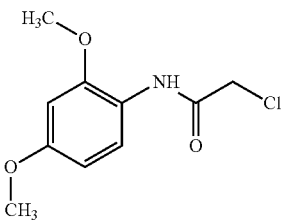
c)

Example 3. Synthesis of 3-[[2-(2,3-dihydro-1H-indol-1-yl)-2-oxoethyl]thio]-N-(2-methylphenyl)-9H-1,2,4-Triazol[4,3-a]benzimidazole-9-acetamide of formula (III)

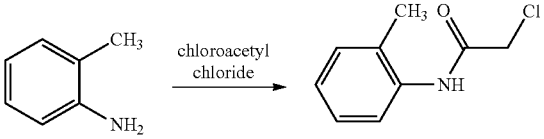
a) b)

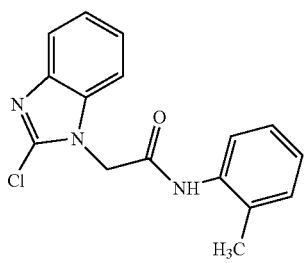
d)

a) was reacted in MeCN with chloroacetyl chloride at reflux to give b) which was then reacted with 2-chloro-1H-benzimidazole in K$_2$CO$_3$, DMF to give d). d) was then reacted with NH$_2$NH$_2$*H$_2$O in EtOH to give e) that, reacted with 2-chloro-1-(1,3-dihydro-2H-isoindol-2-yl)ethanone, lead to the obtainment of the desired 3-[[2-(2,3-dihydro-1H-indol-1-yl)-2-oxoethyl]thio]-N-(2-methylphenyl)-9H-1,2,4-Triazol[4,3-a]benzimidazole-9-acetamide.

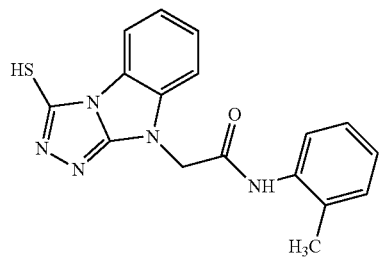

e)

Example 4. Molecular Database Preparation

The Asinex Platinum Collection (http://www.asinex.com/download-zone.html) is a lead-like structural library containing approx. 130,000 in-house synthesized compounds.

The SD file containing all the structures was downloaded and a single low-energy conformation for each putative ligand contained in the Asinex SD file was produced.

Example 5. Molecular Docking

The in silico screening was carried out with a molecular docking approach. 1,000 conformations were generated for each ligand by sampling their rotable bonds. The selected placement methodology was carried out by superposing triplets of ligand atoms and triplets of receptor site points. Before scoring all the generated poses, duplicate complexes were removed. The accepted poses were scored according to the London dG scoring, which estimates the free energy of binding of the ligand from a given pose. All the ligands contained in the Platinum library were screened according to the above procedure. The 15 top scoring compounds were resubmitted to the same docking procedure, keeping for each one of them 300 poses. The estimated binding affinity and the ligand efficiency were calculated, and the pKi was computed through the binding free energy estimated with the London dG scoring function. Data related to the docking energy obtained for a panel of compound tested in silico on the CXCR4 structural model are reported in Table 1. In the first section of the table, data referred to compounds belonging to the three family of compounds here claimed are reported. In the second section, data referred to compounds that do not share the claimed structures are reported. For this second group of compounds, the docking energy is considerably higher than that observed for the first group of compound, meaning a low affinity for the receptor.

TABLE 1

| Compound | Docking score |
|---|---|
| Compounds of formula (I) | |
| N-[4-[5-[[2-[(4-chlorophenyl)amino]-2-oxoethyl]thio]-4-methyl-4H-1,2,4-triazol-3-yl]phenyl]-benzamide | −32.569 |
| N-Phenyl-2-(5-m-tolyl-2H-[1,2,4]triazol-3-ylsulfanyl)-acetamide | −7,295 |
| 2-(5-m-Tolyl-2H-[1,2,4]triazol-3-ylsulfanyl)-acetamide | −9,987 |
| N-Naphthalen-1-yl-2-(5-m-tolyl-2H-[1,2,4]triazol-3-ylsulfanyl)-acetamide | −18,409 |
| N-Thiazol-2-yl-2-(5-p-tolyl-4H-[1,2,4]triazol-3-ylsulfanyl)-acetamide | −14,440 |
| N-(2-Methyl-3H-benzoimidazol-5-yl)-2-(5-phenyl-4H-[1,2,4]triazol-3-ylsulfanyl)-acetamide | −5,990 |
| Compounds of formula (II) | |
| 1H-1,5-N-(2,4-dimethoxyphenyl)-2,3-dihydro-2-oxo-4-phenyl benzodiazepine-1-acetamide | −32.200 |
| N-Benzyl-2-(2-oxo-4-phenyl-2,3-dihydro-benzo[b][1,4]diazepin-1-yl)-acetamide | −8,498 |
| N-(2,3-Dimethyl-phenyl)-2-(2-oxo-4-phenyl-2,3-dihydro-benzo[b][1,4]diazepin-1-yl)-acetamide | −29.188 |
| N-(2,6-Dimethyl-phenyl)-2-(2-oxo-4-phenyl-2,3-dihydro-benzo[b][1,4]diazepin-1-yl)-acetamide | −24,581 |
| Compounds of formula (III) | |
| 3-[[2-2,3-dihydro-1H-indol-1-yl)-2-oxoethyl]thio]-N-(2-methylphenyl)-9H-1,2,4-Triazol[4,3-a]benzimidazole-9-acetamide | −35.597 |
| 2-[9-(4-Chloro-benzyl)-9H-benzo[4,5]imidazo[2,1-c][1,2,4]triazol-3-ylsulfanyl]-1-(3,4-dihydro-1H-isoquinolin-2-yl)-ethanone | −24.021 |
| 2-(9-Benzyl-9H-benzo[4,5]imidazo[2,1-c][1,2,4]triazol-3-ylsulfanyl)-1-pyrrolidin-1-yl-ethanone | −23,531 |
| 2-[9-(4-Chloro-benzyl)-9H-benzo[4,5]imidazo[2,1-c][1,2,4]triazol-3-ylsulfanyl]-1-pyrrolidin-1-yl-ethanone | −22,275 |
| 1-(3,4-Dihydro-2H-quinolin-1-yl)-2-(6,8-dimethyl-9H-1,3,4,9-tetraaza-fluoren-2-ylsulfanyl)-ethanone | −21,426 |
| 2-[3-(2-Oxo-2-piperidin-1-yl-ethylsulfanyl)-benzo[4,5]imidazo[2,1-c][1,2,4]triazol-9-yl]-1-pyrrolidin-1-yl-ethanone | −21,251 |
| 2-(9-Benzyl-9H-benzo[4,5]imidazo[2,1-c][1,2,4]triazol-3-ylsulfanyl)-1-(2,3-dihydro-indol-1-yl)-ethanone | −20,713 |
| 2-(9-Benzyl-9H-benzo[4,5]imidazo[2,1-c][1,2,4]triazol-3-ylsulfanyl)-1-piperidin-1-yl-ethanone | −20,700 |
| 2-[9-(4-Methyl-benzyl)-9H-benzo[4,5]imidazo[2,1-c][1,2,4]triazol-3-ylsulfanyl]-1-(4-methyl-piperidin-1-yl)-ethanone | −19,385 |
| 2-{3-[2-(3,4-Dihydro-2H-quinolin-1-yl)-2-oxo-ethylsulfanyl]-benzo[4,5]imidazo[2,1-c][1,2,4]triazol-9-yl}-1-pyrrolidin-1-yl-ethanone | −17,248 |
| 2-[9-(2-Chloro-benzyl)-9H-benzo[4,5]imidazo[2,1-c][1,2,4]triazol-3-ylsulfanyl]-1-pyrrolidin-1-yl-ethanone | −17,126 |
| 2-{3-[2-2,3-Dihydro-indol-1-yl)-2-oxo-ethylsulfanyl]-benzo[4,5]imidazo[2,1-c][1,2,4]triazol-9-yl}-pyrrolidin-1yl-ethanone | −14,847 |
| 1-(2,3-Dihydro-indol-1-yl)-2-]-(4-methyl-benzyl)-9H-benzo[4,5]imidazo[2,1-c][1,2,4]triazol-3-ylsulfanyl]-ethanone | −13,766 |
| 2-{3-[2-(3,4-Dihydro-1H-isoquinolin-2-yl)-2-oxo-ethylsulfanyl]-benzo[4,5]imidazo[2,1-c][1,2,4]triazol-9-yl}-1-pyrrolidin-1yl-ethanone | −13,030 |
| 1-(3,4-Dihydro-2H-quinolin-1-yl)-2-[9-(4-fluoro-benzyl)-9H-benzo[4,5]imidazo[2,1-c][1,2,4]triazol-3-ylsulfanyl | −12,962 |
| 2-[9-(2-Fluoro-benzyl)-9H-benzo[4,5]imidazo[2,1-c][1,2,4]triazol-3-ylsulfanyl]-1-pyrrolidin-1-yl-ethanone | −12,758 |

TABLE 1-continued

| Compound | Docking score |
|---|---|
| N-Cyclohexyl-2-[3-(2-oxo-2-pyrrolidin-1-yl-ethylsulfanyl)-benzo[4,5]imidazo[2,1-c][1,2,4]triazol-9-yl]-acetamide | −12,439 |
| 2-[9-(4-Fluoro-benzyl)-9H-benzo[4,5]imidazo[2,1-c][1,2,4]triazol-3-ylsulfanyl]-1-pyrrolidin-1-yl-ethanone | −12,181 |
| 2-(9-Benzyl-9H-benzo[4,5]imidazo[2,1-c][1,2,4]triazol-3-ylsulfanyl)-1-(3,5-dimethyl-piperidin-1-yl)-ethanone | −11,970 |
| 2-[9-(4-Methyl-benzyl)-9H-benzo[4,5]imidazo[2,1-c][1,2,4]triazol-3-ylsulfanyl[-1-(3-methyl-piperidin-1-yl)-ethanone | −10,300 |
| 2-[9-(4-Methyl-benzyl)-9H-benzo[4,5]imidazo[2,1-c][1,2,4]triazol-3-ylsulfanyl]-N-(2-piperidin-1-yl-phenyl)-acetamide | −8,359 |
| 2-(9-Benzyl-9H-benzo[4,5]imidazo[2,1-c][1,2,4]triazol-3-ylsulfanyl)-N-(2-piperidin-1-yl-phenyl)-acetamide | −23.545 |
| Other compounds | |
| Benzenesulfonamide, 4-chloro-N-[(5,6-dihydro-6-oxo-1,3-dioxolo[4,5-g]quinolin-7-yl)methyl]-N-[(tetrahydro-2-furanyl)methyl]- | 208.559 |
| Propanamide,N-[4-[[2-[(8,9,10,11 tetrahydro[1]benzothieno[3,2-e]-1,2,4-triazolo[4,3-c]pyrimidin-3-yl)thio]acetyl]amino]phenyl] | 223.048 |
| Acetamide,N-(5-methyl-3-isoxazolyl)-2-[(8,9,10,11-tetrahydro-5-methyl[1]benzothieno[3,2-e]-1,2,4-triazolo[4,3-c]pyrimidin-3-yl)thio]- | 253.290 |
| Acetamide,N-[4-(1,1-dimethylethyl)-2-thiazolyl]-2-[(5-ethyl-8,9,10,11-tetrahydro[1]benzothieno[3,2-e]-1,2,4-triazolo[4,3-c]pyrimidin-3-yl)thio]- | 253.916 |

BIBLIOGRAPHY

Abbracchio M P (2006) EMBO J 25:4615.
Abbracchio M P, Burnstock G, Boeynaems J M, Barnard E A, Boyer J L, Kennedy C, Knight G E, Fumagalli M, Gachet C, Jacobson K A, Weisman G A (2006) Pharmacol Rev. 58(3):281-341.
Abbracchio M P, Burnstock G, Verkhratsky A, Zimmermann H (2009) Trends Neurosci. 32(1):19-29.
Brink C (2003) Adv Exp Med Biol 525:7.
Calleri E, Ceruti S, Cristalli G, Martini C, Temporini C, Parravicini C, Volpini R, Daniele S, Caccialanza G, Lecca D, Lambertucci C, Trincavelli M L, Marucci G, Wainer I W, Ranghino G, Fantucci P, Abbracchio M P, Massolini G (2010) J Med Chem 53:3489.
Ceruti S, Villa G, Genovese T, Mazzon E, Longhi R, Rosa P, Bramanti P, Cuzzocrea S, Abbracchio M P (2009) Brain 132:2206.
Chen Y, Wu H, Wang S, Koito H, Li J, Ye F, Hoang J, Escobar S S, Gow A, Arnett H A, Trapp B D, Karandikar N J, Hsieh J, Lu Q R (2009) Nat Neurosci 12:1398.
Ciana P, Fumagalli M, Trincavelli M L, Verderio C, Rosa P, Lecca D, Ferrario S, Parravicini C, Capra V, Gelosa P, Guerrini U, Belcredito S, Cimino M, Sironi L, Tremoli E, Rovati G E, Martini C, Eberini I, Daniele S, Parravicini C, Sensi C, Trincavelli M L, Martini C, Abbracchio M P (2011) J Comput Aided Mol Des 25:743:752.
Fumagalli M, Daniele S, Lecca D, Lee P R, Parravicini C, Fields R D, Rosa P, Antonucci F, Verderio C, Trincavelli M L, Bramanti P, Martini C, Abbracchio M P (2011) J Biol Chem. 286(12):10593-604.
Lecca D, Trincavelli M L, Gelosa P, Sironi L, Ciana P, Fumagalli M, Villa G, Verderio C, Grumelli C, Guerrini U, Tremoli E, Rosa P, Cuboni S, Martini C, Buffo A, Cimino M, Abbracchio M P (2008) PLoS One 3:e3579.
Pugliese A M, Trincavelli M L, Lecca D, Coppi E, Fumagalli M, Ferrario S, Failli P, Daniele S, Martini C, Pedata F, Abbracchio M P (2009) Am J Physiol Cell Physiol 297:C1028. Wojciechowski M, Lesyng B (2004) J. Phys. Chem. B 108:18368.
Wu B, Chien E Y, Mol C D, Fenalti G, Liu W, Katritch V, Abagyan R, Brooun A, Wells P, Bi F C, Hamel D J, Kuhn P, Handel T M, Cherezov V, Stevens R C (2010) Science 330:1066.

The invention claimed is:

1. A method of treating or ameliorating multiple sclerosis comprising administering the compound of Formula I

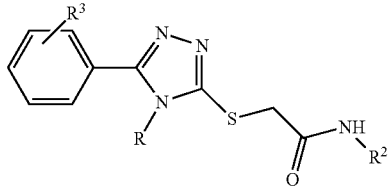

(I)

wherein R is selected from the group consisting of: H, a linear or branched C1-C4 alkyl, a linear or branched C1-C4 alkyl phenyl, a phenyl;
R² is selected from the group consisting of: H, a linear or branched C1-C4 alkyl, a saturated or unsaturated mono, bi or tricycle having from 3 to 16 carbon members, 4Cl-phenyl, a saturated or unsaturated mono, bi or tricycle having from 3 to 16 members containing from 1 to 4 heteroatoms selected from N, O, S, 2-methyl-benzimidazole; and
R³ is selected from the group consisting of: H, a linear or branched C1-C4 alkyl or NHC(O)R¹, wherein R¹ is selected from the group consisting of: a linear or branched C1-C4 alkyl, a saturated or unsaturated mono, bi or tricycle having from 3 to 16 carbon members, a substituted saturated or unsaturated mono, bi or tricycle having from 3 to 16 members wherein said substituents are independently selected from C1-C4 linear or branched alkyl, acetyl, C1-C4 alkoxy, carboxy C1-C4 alkyl, F, Cl, Br, I, trifluoromethyl, nitro, CN; a saturated or unsaturated mono, bi or tricycle having from 3 to 16 members containing from 1 to 4 heteroatoms selected from N, O, S; a substituted saturated or unsaturated mono, bi or tricycle having from 3 to 16 members wherein said substituents are independently selected from C1-C4 linear or branched alkyl, acetyl, C1-C4 alkoxy, carboxy C1-C4 alkyl, F, Cl, Br, I, trifluoromethyl, nitro, CN and having from 1 to 4 heteroatoms selected from N, O, S or a pharmacologically acceptable salt thereof and a pharmaceutically acceptable carrier.

2. A method of treating or ameliorating multiple sclerosis according to claim 1, wherein in said compound of formula (I)
R is selected from the group consisting of: H, methyl, ethyl, phenyl, benzyl;
R² is selected from the group consisting of: H, naphthalene, phenyl, 4Cl-phenyl, benzimidazole, 2-methyl-benzimidazole, thiazole; and R³ is selected from the group consisting of: H, 4-methyl, 4-NHC(O)R¹, wherein R¹ is phenyl or phenyl mono, bio tri substituted, wherein said substituents on said phenyl are independently selected from C1-C4 linear or branched alkyl, acetyl, C1-C4 alkoxy, carboxy C1-C4 alkyl, F, Cl, Br, I, trifluoromethyl, nitro, CN or a pharmacologically acceptable salt thereof.

3. A method of treating or ameliorating multiple sclerosis according to claim 1, wherein in said compound of formula (I)
R is H or methyl;
R² is H, naphthalene, phenyl, 4Cl-phenyl, benzimidazole, 2-methylbenzimidazole, thiazole; and
R³ is H, 4-methyl, 4-NHC(O)R¹,
wherein R¹ is phenyl or 4Cl-phenyl.

4. A method of treating or ameliorating multiple sclerosis according to claim 1, wherein in said compound of formula (I) is selected from the group consisting of:
N-Phenyl-2-(5-m-tolyl-2H-[1,2,4]triazol-3-ylsulfanyl)-acetamide,
2-(5-m-tolyl-2H-[1,2,4]triazol-3-ylsulfanyl)-acetamide,
N-naphthalen-1-yl-2-(5-m-tolyl-2H-[1,2,4]triazol-3-yl-sulfanyl)-acetamide,
N-Thiazol-2-yl-2-(5-p-tolyl-4H-[1,2,4]triazol-3-ylsulfanyl)-acetamide,
N-(2-Methyl-3H-benzoimidazol-5-yl)-2-(5-phenyl-4H-[1,2,4]triazol-3-ylsulfanyl)-acetamide,
and N-[4-[5-[[2-[(4-chlorophenyl)amino]-2-oxoethyl]thio]-4-methyl-4H-1,2,4-triazol-3-yl]phenyl]-benzamide.

* * * * *